United States Patent
Schuster et al.

(10) Patent No.: US 7,759,464 B2
(45) Date of Patent: Jul. 20, 2010

(54) N-GLYCOSYLATED ANTIBODY

(75) Inventors: Manfred Schuster, Schrick (AT); Gottfried Himmler, Vienna (AT); Gunter Waxenecker, Mank (AT); Geert C. Mudde, Breitenfurt (AT); Manuela Loidl, Korneuburg (AT); Gerda Redl, Rutzendorf (AT); Hans Loibner, Vienna (AT)

(73) Assignees: Greenovation Biotech GmbH, Freiburg (DE); Meridian Biopharmaceuticals GmbH, Vienna (AT)

( * ) Notice: Subject to any disclaimer, the term of this patent is extended or adjusted under 35 U.S.C. 154(b) by 503 days.

(21) Appl. No.: 11/571,983

(22) PCT Filed: Jul. 14, 2004

(86) PCT No.: PCT/EP2004/007787

§ 371 (c)(1),
(2), (4) Date: Jan. 11, 2007

(87) PCT Pub. No.: WO2006/005367

PCT Pub. Date: Jan. 19, 2006

(65) Prior Publication Data

US 2008/0095783 A1    Apr. 24, 2008

(51) Int. Cl.
*C07K 16/00* (2006.01)
*A61K 39/395* (2006.01)
(52) U.S. Cl. .................. 530/388.1; 424/141.1
(58) Field of Classification Search .......... None
See application file for complete search history.

(56) References Cited

FOREIGN PATENT DOCUMENTS

| EP | 0528767 | 2/1993 |
|---|---|---|
| EP | 1140168 | 10/2001 |
| EP | 1176195 | 1/2002 |
| WO | WO-03/011878 | 2/2003 |
| WO | WO-2004/009782 | 1/2004 |
| WO | WO-2004/024871 | 3/2004 |

OTHER PUBLICATIONS

Kitamura et al., Proc. Natl. Acad. Sci. USA, 1994, 91: 12957-12961.*
Van Der Kolk, L. E. et al., "Complement activation plays a key role in the side-effects of rituximab treatment," British Journal of Haematology, 2001, vol. 115, p. 807-811.
Casadevall, Arturo et al., "Return to the past: The case for antibody-based therapies in infectious diseases," Clinical Infectious Diseases, 1995, vol. 21, pp. 150-161.
Chippaux, J.P. et al., "Venoms, antivenoms and immunotherapy," Toxicon, 1998, vol. 36, No. 6, pp. 823-846.
Barachi, Joseph J. Jr., "Emerging roles of carbohydrates and glycomimetics in anticancer drug design," Current Pharmaceutical Design, 200, vol. 6, pp. 485-501.
Glennie, Martin J. et al., "Clinical trials of antibody therapy," Immunology Today, Aug. 2000, vol. 21, No. 8, pp. 403-410.
Gollogly, L. et al., "A possible role for the alpha 1—3 galactosyl epitope and the natural anti-gal antibody in oncogenesis," Neoplasma, 1996, vol. 43, No. 5, pp. 285-289.
Lifely, Robert M. et al., "Glycosylation and biological activity of CAMPATH-1H expressed in different cell lines and grown under different culture conditions," Glycobiology, 1995, vol. 5, No. 8, pp. 813-822.
Miyake, Masayuki et al., "Correlation of expression of H/LeY/Le$^b$ antigens with survival in patients with carcinoma of the lung," The New England Journal of Medicine, Jul. 2, 1992, vol. 327, No. 1, pp. 14-18.
Miyoshi, Eiji et al., "Transfection of N-acetylglucosaminyltransferase III gene suppresses expression of hepatitis B virus in a human hepatoma cell Line, HB611," The Journal of Biological Chemistry, Nov. 24, 1995, vol. 270, No. 47, pp. 28311-28315.
Sabouraud, A. et al., "Immunotherapie des intoxications medicamenteuses," Therapie, 1994 vol. 49, pp. 41-48.
Sburlati, Adriana R. et al., "Synthesis of bisected glycoforms of recombinant IFN-β by overexpression of β-1,4-N-acetylglucosaminyltransferase III in chinese hamster ovary cells," Biotechnol. Prog., 1998, vol. 14, pp. 189-192.
Scott, Andrew et al., "Antibody-based immunological therapies," Current Opionion in Immunology, 1997, vol. 9, pp. 717-722.
Lewis, Jonathan J. et al., "Definition of tumor antigens suitable for vaccine construction," Seminars in Cancer Biology, 1995, vol. 6, pp. 321-327.
Shinkawa, Toyohide et al., "The absence of fucose but not the presence of galactose or bisecting N-acetylglucosamine of human IgG1 complex-type oligosaccharides shows the critical role of enhancing antibody-dependent cellular cytotoxicity," The Journal of Bilogical Chemistry, Jan. 31, 2003, vol. 278, No. 5, pp. 3466-3473.
Lund, John et al., "Multiple interaction of IgG with its core oligosaccharide can modulate recognition by complement and human Fcγ receptor I and influence the synthesis of its oligosaccharide chains," The Journal of Immunology, 1996, vol. 157, pp. 4963-4969.
Davies, J. et al., "Expression of GnTIII in a recombinant anti-CD20 CHO production cell line: Expression of antibodies with altered glycoforms leads to an increase in ADCC through higher affinity for FC gamma RIII," Biotechnology and Bioengineering—Combinatorial Chemistry, Wiley, New York, NY, US, Aug. 20, 2001, vol. 74, No. 4, pp. 288-294.
Umana, P. et al., "Engineered glycoforms of an antineuroblastoma IGG1 with optimized antibody-dependent cellular cytotoxic activity," Nature Biotechnology, Feb. 1999, vol. 17, pp. 176-180.

* cited by examiner

*Primary Examiner*—Ilia Ouspenski
(74) *Attorney, Agent, or Firm*—Birch, Stewart, Kolasch & Birch, LLP

(57) ABSTRACT

The invention relates to a monoclonal antibody, or fragment of the antibody, that is derived from a parental monoclonal antibody, that recognizes the Lewis Y antigen, characterized in that the Fc region of the antibody, or fragment of the antibody, carries a bi-sected hybrid type N-glycosylation pattern and that the antibody shows at least 10 fold increased ADCC and at least 10% reduced CDC activity.

12 Claims, 3 Drawing Sheets

DIVMTQSPLS LPVTPGEPAS ISCRSSQSIV HSNGNTYLEW
YLQKPGQSPQ LLISKVSNRF SGVPDRFSGS GSGTDFTLKI
SRVEAEDVGV YYCFQGSHVP FTFGQGTKLE IK

Fig. 1

Seq. 1:
EVQLLESGGG LVQPGGSLRL SCAASGFTFS DYYMYWVRQA
PEKRLEWVAY ISNGGGSSHY VDSVKGRFTI SRDNSKNTLY
LQMNSLRAED TALYHCARGM DYGAWFAYWG QGTLVTVSS

Seq. 2:
EVQLLESGGG LVQPGGSLRL SCAASGFTFS DYYMYWVRQA
PEKRLEWVAY ISNGGGSSHY VDSVKGRFTI SRDNAKNTLY
LQMNSLRAED TALYHCARGM DYGAWFAYWG QGTLVTVSS

Fig. 2

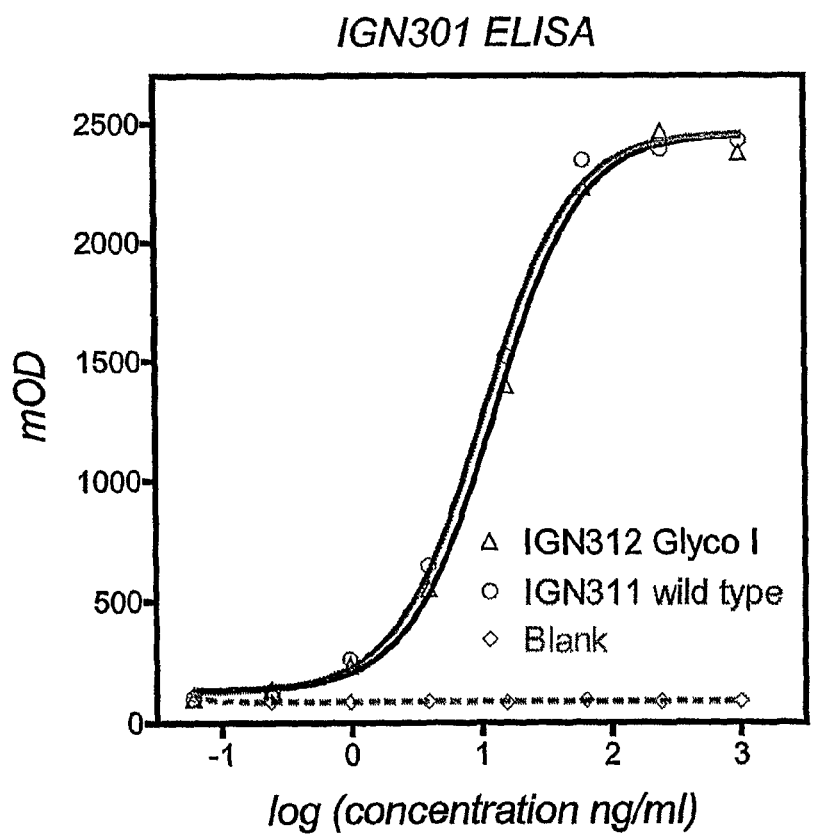

Fig. 3

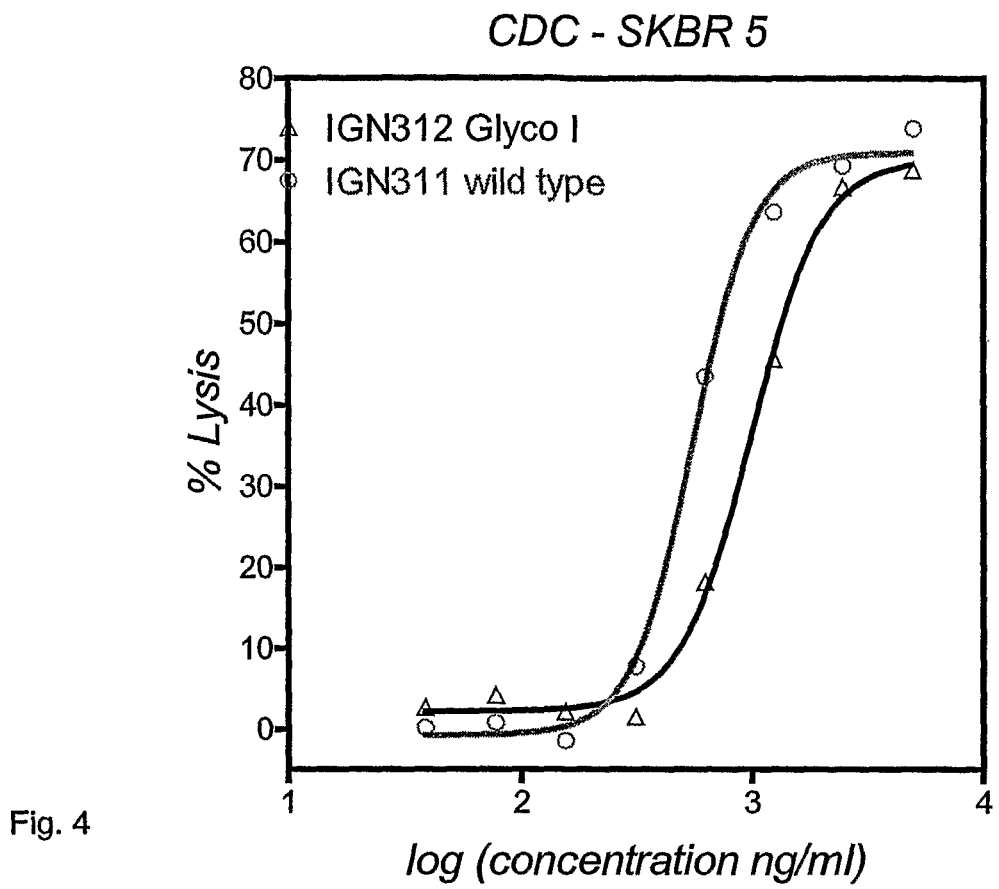
Fig. 4
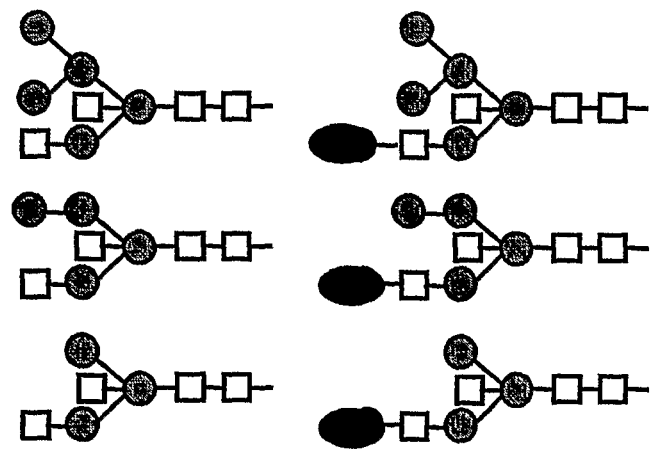
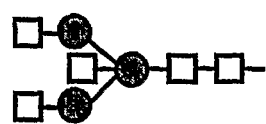
Fig. 6

SEQUENCE LISTING

<160> NUMBER OF SEQ ID NOS: 3

<210> SEQ ID NO 1
<211> LENGTH: 112
<212> TYPE: PRT
<213> ORGANISM: Artificial
<220> FEATURE:
<223> OTHER INFORMATION: Sequence of humanized light chain variable region

<400> SEQUENCE: 1

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Ser Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gln Gly Thr Lys Leu Glu Ile Lys
            100                 105                 110
```

<210> SEQ ID NO 2
<211> LENGTH: 119
<212> TYPE: PRT
<213> ORGANISM: Artificial
<220> FEATURE:
<223> OTHER INFORMATION: sequence of humanized heavy chain variable region

<400> SEQUENCE: 2

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Glu Lys Arg Leu Glu Trp Val
        35                  40                  45

Ala Tyr Ile Ser Asn Gly Gly Ser Ser His Tyr Val Asp Ser Val
    50                  55                  60
```

```
-continued

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr His Cys
                85                  90                  95

Ala Arg Gly Met Asp Tyr Gly Ala Trp Phe Ala Tyr Trp Gly Gln Gly
            100                 105                 110

Thr Leu Val Thr Val Ser Ser
        115

<210> SEQ ID NO 3
<211> LENGTH: 119
<212> TYPE: PRT
<213> ORGANISM: Artificial
<220> FEATURE:
<223> OTHER INFORMATION: sequence of humanized heavy chain variable
      region

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Glu Lys Arg Leu Glu Trp Val
        35                  40                  45

Ala Tyr Ile Ser Asn Gly Gly Gly Ser Ser His Tyr Val Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Leu Tyr His Cys
                85                  90                  95

Ala Arg Gly Met Asp Tyr Gly Ala Trp Phe Ala Tyr Trp Gly Gln Gly
            100                 105                 110

Thr Leu Val Thr Val Ser Ser
        115
```

N-GLYCOSYLATED ANTIBODY

The invention relates to a novel N-glycosylated antibody or derivative thereof carrying a bi-sected hybrid type N-glycosylation pattern and having increased ADCC and decreased CDC activities.

The invention also relates to the use of the antibodies for the preparation of medicaments for the treatment of cancer.

Tumors are formed due to the unchecked cell growth which leads to the formation of solid cell agglomerates in case of epithelial cells. In case of benign tumor tissue, it is assumed that the cell growth is limited and secondary tumors or metastases will not occur. In cancer diseases, however, malignant tumors form, and in the progressing stage secondary tumors and metastases occur. Most frequently, cancer forms with epithelial tumors occur which inter alia concern breast, stomach, intestines, pancreas, lungs, prostate and ovaries.

Cancer is a wide-spread disease and is lethal in many cases. The therapy of cancer usually comprises the removal of a solid tumor, and a further treatment which is to prevent and reduce, respectively, metastases. Besides surgery, the standard therapies include chemotherapy and radiation therapy. Despite the comprehensive therapy which often involves severe side effects, the success of treatment is insufficient. The relapse rate in intestinal cancer is approximately 45%. Metastatic epithelial cancer is considered to be nearly incurable. Therefore, in the treatment of cancer patients it is important to prevent, and reduce, respectively, the formation of metastases.

Tumor cells are capable of disseminating from primary tumors in body liquids and other organs. These disseminated tumor cells may be in their dormant state and often cannot be attacked by a chemotherapy (radiotherapy). Such a treated patient seems to be in a cured state. Dormant tumor cells, however, have a potential of forming metastases if they become growing and metastasizing cells, described as "minimal residual disease".

Immunotherapy constitutes an innovative possible treatment of cancer patients. Both active and also passive immunotherapy are acknowledged measures for supporting the immune system.

The adaptive immune system of humans consists of two essential components, the humoral and the cellular immunity. The adaptive immune response partially is based on the clonal selection of B- and T-lymphocytes and in principle allows for the recognition of any desired antigen as well as for the build-up of an immunological memory. These characteristics of the adaptive immune system are generally usefully addressed in vaccinations.

Each B-cell produces an antibody with a defined binding specificity. This antibody is also present as a specific receptor in the membrane of the B-cell producing it. The humoral immune response against antigens recognized as foreign is based on the selective activation of those B-cells which produce such antibodies that can bind to an epitope of the respective antigen. For the antibody diversity, DNA rearrangements in the course of B-cell differentiation play a decisive role.

There are several possible ways of interfering in the immune system.

1. Passive Antibody Therapy:

For therapeutic purposes, it is possible to supply to an organism antibodies required for a certain function within this organism. This type of application is called passive immunotherapy, and it can be used in various medical indications, e.g. in the immunotherapy of cancer (Glennie M. J. and Johnson P. W. M., Immunol. Today (2000), 21:403), intoxications (Chippaux J. P. and Goyffon M., Toxicon (1998), 36:823; Sabouraud A, Scherrmann J M, Therapie (1994), 49:41) and infections (Casadevall A and Scharff M. D., Clin. Infect. Dis. (1995), 21:150). In these cases, antibodies can be used which either have been derived from appropriately immunized animals or can be recovered from cells by various biological or molecular-biological techniques (e.g. hybridoma technique, phage-display technique, etc.) via the immortalization of immunoglobulin genes.

2. Active Immunization:

To modulate the immune system, an immunization with antigens can be used. Antigens are molecules, molecule complexes or whole organisms to which antibodies can bind. Not all the antigens induce an immune response, i.e. not all the antigens are immunogenic. Certain small molecules are not registered by the immune system (haptens), such smaller molecules can be presented to the immune system in suitable form, and thus be made immunogenic. Such a method is the coupling of the hapten to an immunogenic molecule, a so-called carrier molecule. For an active immunization, also antibody preparations can be used, as described in EP 1140168.

Tumor cells can be attacked by the immune system only to a limited extent, since they are hardly different from normal cells and specific antibodies therefore are missing. Much research is directed to the identification of suitable targets, i.e. target antigens, for the preparation of tumor-specific antibodies. The immunotherapy for the treatment of cancer then either comprises the passive therapy by the direct administration of the specific antibodies, or the active vaccination with suitable antigen-targets for stimulating the immune system and generating the specific antibodies in vivo.

One approach of relatively specifically destroying tumor cells is the passive immunotherapy with antibodies directed against tumor-associated antigens (TAA) (Glennie M. J. and Johnson P. W. M., Immunology Today (2000), 21:403-410; Scott A. M. and Welt S., Curr. Opin. Immunol. (1997), 9:717).

Certain TAAs are defined as relevant "targets" for the development of immunotherapeutic agents for the prophylaxis and/or treatment of cancer. TAAs are structures which preferably are expressed on the cell membrane of tumor cells, thereby allow for a differentiation relative to non-malignant tissue, and thus can be viewed as targets for the diagnostic and therapeutic applications of specific antibodies.

In the course of the discovery and the subsequent characterization of various TAAs it has been found that they often have important functions for cancer cells. They allow the degenerate cells to have properties characteristic of the malignant phenotype, such as, e.g., an increased adhesion capacity, or an increased uptake of growth factors, which are highly important for establishing metastases. However, in certain stages, such antigens may very well also be expressed on normal cells where they are responsible for normal functions of these cells. An example of this is the Lewis Y carbohydrate antigen which appears on the plurality of tumors of epithelial origin, but also plays an important role during the fetal development of epithelial tissues. It has been shown that the expression of this antigen in lung cancer is associated with an unfavorable prognosis, since Lewis Y positive cancer cells apparently have a higher metastatic potential (Miyake M. et al, N. Engl. J. Med. 327 (1992), 14).

In EP 0 528 767, the use of a humanized anti-Lewis Y antibody for the treatment of epithelial cancer has been described.

Among the further known tumor-associated carbohydrate structures, there are, e.g., all those Lewis antigens which are highly expressed in many types of epithelial cancers. Among them are Lewis x-, Lewis b- and Lewis y-structures, as well as sialylated Lewis x-structures. Other carbohydrate antigens are Globo H-structures, KH1, Tn antigen, TF antigen, the alpha-1,3-galactosyl epitope (Curr. Pharmaceutical Design (2000), 6:485, Gollogly L. and Castronovo V., Neoplasma (1996), 43:285).

Other TAAs are proteins which are particularly highly expressed by cancer cells, such as, e.g. CEA, TAG-72, MUC1, Folate Binding Protein A-33, CA125, EpCAM, HER-2/neu, PSA, MART, etc. (Sem. Cancer Biol. (1995), 6:321). Relevant TAAs often are surface antigens of epithelial cells which occur in larger numbers in growing cells, such as fetal tissue, and also in tumor tissue.

Direct therapeutic applications of antibodies against TAA are based on passive immunotherapies, i.e., a specific antibody is systemically administered in a suitable amount to cancer patients, and has an immunotherapeutic effect. The biological half-life of such agents will depend on their structure and is limited. Therefore, it is necessary to carry out repeated applications. When using xenogenic antibodies (e.g. murine monoclonal antibodies, MABs) however, this can lead to undesired immune reactions which may neutralize a possible therapeutic effect and may cause dangerous side effects (anaphylactic reactions). Therefore, such immunotherapeutic agents can be administered for a limited time only.

A better tolerance is obtained by reducing the xenogenic structures of the antibody and by introducing human structures, e.g. with chimeric or humanized antibodies. Also systems for producing specific human antibodies are being developed. Thus, according to the prior art, certain cell lines, organisms or transgenic animals can produce human antibodies.

Nevertheless, it is often reported that the application of high amounts of antibodies, even if these antibodies are humanized antibodies, can lead to side effects that often are dose dependent. These side effects can be diarrhea, fever, chills, bronchospasm (immediate type allergic reaction, ITAR) etc.

It is well known that antibodies achieve their therapeutic effect through various mechanisms. They can have direct effects in producing apoptosis or programmed cell death. They can block growth factor receptors, effectively arresting proliferation of tumor cells. In cells that express monoclonal antibodies, they can bring about anti-idiotype antibody formation.

Indirect effects include recruiting cells that have cytotoxicity, such as monocytes and macrophages. This type of antibody-mediated cell kill is called antibody-dependent cell mediated cytotoxicity (ADCC). Monoclonal antibodies also bind complement, leading to direct cell toxicity, known as complement dependent cytotoxicity (CDC). In case of ADCC (Antibody Dependent Cell mediated Cytotoxicity), the Fc fragment of the monoclonal antibody binds the Fc receptors found on monocytes, macrophages, granulocytes and natural killer cells. These cells in turn engulf the bound tumor cell and destroy it. Natural killer cells secrete cytokines that lead to cell death, and they also recruit B cells. In case of CDC (Complement Dependent Cytotoxicity) the monoclonal antibody is binding to the receptor and initiating the complement system, also known as the "complement cascade". The end result is a membrane attack complex that literally makes a hole within the cell membrane, causing cell lysis and death. Methods for the production of antibodies having increased ADCC and CDC activities have already been described (Sburlati et al., 1998, Biotechnol. Prog., 14, 189-192; Shinkawa T. et al., 2003, J. Biol. Chem., 278, 3466-3473).

It has been shown that antibody mediated CDC activity can lead to partially severe side effects in antibody therapy. For example, it was described by van der Kolk et al. (British J. Haematol., 2001, 115, 807-811) that the treatment with a chimaeric anti-CD20 antibody lead to moderate to severe side effects which were argued due to complement activation. It was shown that the severity of the side effects correlated with the level of complement activation. Especially in patients with a high number of circulating tumor cells these side effects can be life threatening. The increased toxicity due to complement dependent cytotoxicity was suggested to be carefully examined when the complement activation is enhanced.

Studies on other antibodies (OKT3) supported these observations with regard to the negative side effects induced by complement activation.

Therefore there is a great demand in providing means for antibody therapy that avoids these unwanted side effects.

The object of the invention is to provide antibodies with improved properties.

According to the invention, this object is achieved by the subject matter of the claims.

The present inventors have generated a monoclonal antibody or derivative or fragment thereof that is derived from a parental monoclonal antibody that recognizes the Lewis Y antigen, characterized in that the Fc region or region equivalent to the Fc region of said antibody or derivative or fragment thereof carries a bi-sected hybrid type N-glycosylation pattern and that said antibody shows at least 10 fold increased ADCC and at least 10% reduced CDC activity.

The parental monoclonal antibody that is directed against the Lewis Y antigen is an antibody comprising a humanized light chain variable region, a human light chain constant region, a humanized heavy chain variable region and a human heavy chain constant region, wherein the humanized light chain variable region has an amino acid sequence as shown in FIG. 1 and the humanized heavy chain variable region has the amino acid sequence as shown in FIG. 2. Such antibody is described in EP 0 528 767.

Preferentially the antibody according to the invention contains at least parts of the amino acid sequence of the heavy chain variable region and heavy chain constant region of the parental antibody. Most preferred, the amino acid sequence of the inventive antibody is identical to the parental antibody. Preferably the inventive antibody is directed against the Lewis Y antigen.

The clinical efficacy of the parental antibody is related to the biological activity of the Fc part of the human IgG1 molecule, which is determined by its efficiency in inducing antibody dependent cellular cytotoxicity (ADCC) and complement dependent cytotoxicity (CDC). Especially the ADCC function depends on the glycosylation of the Fc part, which interacts with the FcγRIII on granulocytes and monocytes (Lifely et al., 1995, Glycobiology, 5(8), 813-822).

Oligosaccharides normally found in the Fc region of serum IgG are complex bi-antennary type with low levels of terminally sialic acid and bisecting N-acetylglycosamine and a variable degree of terminal galactosylation and core fucosylation (Lund and Takahashi, 1996, J. Immunol., 157, 4963-9). FcγR binding requires the presence of oligosaccharides covalently attached at the conserved Asn297 in the Fc region and is sensitive to oligosaccharide structure. IgG's expressed in hamster or mouse cell lines carry usually very similar glycosylation structures but lack the bisecting N-acetylglucosamine (GlcNac) found in low amounts in serum IgG.

The ADCC activity of the antibody according to the invention is at least 10 fold increased, preferably at least 20 fold, more preferably at least 25 fold increased ADCC activity, preferably at least 40 fold increased ADCC activity, preferably at least 60 fold increased ADCC activity, most preferred at least 100 fold increased ADCC activity compared to the ADCC activity of the parental antibody.

The ADCC lysis activity of the inventive antibody can be measured in comparison to the parental antibody using six Lewis-Y positive target cancer cell lines (SKBR5, SKBR3, LoVo, MCF7, OVCAR3 and Kato III).

According to the invention, the antibody or derivative or fragment thereof has a CDC activity that is at least 10% decreased, or at least 20% decreased, or at least 40% decreased compared to the CDC activity of the parental antibody.

The antibody according the invention or derivative or fragment therof can either contain a core fucosylation or no fucosylation. It can be a murine, chimeric, human or humanized antibody, preferably the antibody is a humanized one. In a preferred embodiment, the antibody is IgG or a fragment or derivative therof, preferably IgG1 or a fragment or derivative thereof. In a further embodiment, the present inventive antibody is a fusion protein that includes a region equivalent to the Fc region of human IgG.

Accordingly, in one aspect the claimed invention is also directed to a pharmaceutical preparation containing the antibody according to the invention in a pharmaceutically acceptable carrier or diluent.

Furthermore, the use of this antibody as a pharmaceutical is claimed.

The pharmaceutical can be used as medicament for the prophylactic and/or therapeutic treatment for the reduction or inhibition, respectively, of the growth of tumor cells in a patient, especially for the treatment of solid cancer, exemplary for the treatment of tumors or disseminated tumor cells of epithelial origin. Furthermore, the antibody according to the invention can be used for the treatment of minimal residual disease.

Terms as used herein as generally used in the art, unless otherwise defined as follows.

The term "antibody" includes antibodies or antibody derivatives or fragments thereof. Among the antibody fragments are functional equivalents or homologues of antibodies including any polypeptide comprising an immunoglobulin binding domain or peptides mimicking this binding domain together with a Fc region or a region homologous to a Fc region or at least part of it. Chimeric molecules comprising an immunoglobulin binding domain, or equivalents, fused to another polypeptide are included. Exemplary antibody molecules are intact immunoglobulin molecules and those portions of an immunoglobulin molecule that contains the paratope, including those portions known as Fab, Fab', F(ab')2, Fc and F(v).

As used herein, the antibody according to the invention can be expressed in host cells which cover any kind of cellular system which can be modified to express the antibody. Within the scope of the invention, the term "cells" means the cultivation of individual cells, tissues, organs, insect cells, avian cells, mammalian cells, hybridoma cells, primary cells, continuous cell lines, stem cells and/or genetically engineered cells, such as recombinant cells expressing a glycosylated antibody according to the invention.

Preferably the cells are animal cells, more preferably mammalian cells. These can be for example BSC-1 cells, LLC-MK cells, CV-1 cells, CHO cells, COS cells, murine cells, human cells, HeLa cells, 293 cells, VERO cells, MDBK cells, MDCK cells, MDOK cells, CRFK cells, RAF cells, TCMK cells, LLC-PK cells, PK15 cells, WI-38 cells, MRC-5 cells, T-FLY cells, BHK cells, SP2/0, NS0 cells or derivatives thereof.

The bi-sected hybrid type N-glycosylation pattern of the inventive antibody can be produced by a glycoprotein modifying glycosyl transferase, for example the β(1,4)-N-acetyl-glucosaminyltransferase (GlcNAc transferase III, GntIII) which adds the residue. The Gnt III has already been cloned (Miyoshi et al., 1995, J. Biol. Chem., 270:28311-28315). This can result in an antibody that carries a bi-secting N-acetylglucosamine group in the Fc part. The glycosylation of the Fc part of the inventive antibody can be amended by using technologies well known in the art. Exemplary, methods are described in Sburlati et al., 1998, Biotechnol. Prog., 14, 189-192 or U.S. Pat. No. 6,602,684. Herein cells are capable of expressing the Gnt III activity which can increase complex N-linked oligosaccharides carrying bisected GlcNAc. Although most of the cell lines used for production of antibodies do not contain the GntIII enzyme, there are also cells that naturally express the Gnt III enzyme, for example Y0 myeloma cells or B lymphozytes.

A change in the glycosylation pattern can also be induced in host cells by mutational techniques, for example mismatch repair system changes (WO 04/09782, WO 04/24871).

A further technique for the amendment of the glycosylation pattern of the Fc part of the inventive antibody is described in EP 1 176 195.

The term "antibody dependent cellular cytotoxicity" (ADCC) used herein refers to any activity to injury a tumor cell or the like by activating an effector cell via the binding of the Fc region of an antibody to an Fc receptor existing on the surface of an effector cell such as a killer cell, a natural killer cell, an activated macrophage or the like. An antibody having increased ADCC activity can be determined by any suitable method known by the skilled person. An accepted assay is described in the examples.

Increased ADCC can be measured by an increased lytic potential measured as a decreased EC50 antibody concentration which indicates the antibody concentration necessary to specifically lyse the half-maximal amount of target cells.

The term "complement dependent cytotoxicity" (CDC) is defined as direct cell toxicity by binding and activation of complement. An antibody is binding to its target on the cell surface of e.g. the tumor cell and initiates the complement system, also known as "complement cascade" resulting in a membrane attack complex that literally makes a hole within the cell membrane, causing cell lysis and death. An antibody having decreased CDC activity can be determined by any suitable method known by the skilled person. An accepted assay is described in the examples.

Decreased CDC activity can be defined as an increased EC50 antibody concentration which enables the lysis of the half-maximal amount of target cells.

Core fucosylation of an N-linked oligo-saccharide means the presence of a Fucose group linked α-1,6 linked to the Asn neighboring Glc-Nac group.

The binding activity of the inventive antibody to the Lewis y antigen is at least 80% compared to the parental antibody, preferentially at least 90%, more preferentially 100%.

The assembling of constant and light chains of the inventive glycosylated antibody is similar to the parental antibody.

Surprisingly, it was also shown that the N-linked antibody glycosylation pattern according to the invention shows higher homogeneity due to a decreased amount of found oligo-saccharide structures compared to the parental antibody. This leads to the preferred effect that variation between newly produced batches of the antibody is reduced and therefore a more stable and more homogenous antibody preparation is obtained.

A possible treatment objective is the effective binding and reduction of tumor cells, i.e. tumor tissue or metastases or, in particular, disseminated tumor cells. The number of tumor cells, or micrometastases, respectively, detectable in blood, bone marrow or organs shall be significantly reduced. The formation of metastases is to be retarded, their growth is at least to be slowed down. Thus, the relapse-free life span and thus also the total survival time of the patients can be lengthened by the specifically targeted immunotherapy.

Within the scope of the use according to the invention, in particular the treatment for reducing, or inhibiting, respectively, the growth of tumor cells in a cancer patient, also a hemodialysis is possible.

For binding all the glycosylated receptors of a tumor cell, usually a high doses of at least 50 mg/dose, preferably at least 100 mg/dose, most preferred at least 200 mg/dose per patient is administered. The maximum dose will depend on the tolerability of the antibody, humanized antibodies, and human antibodies, respectively, being best tolerated. A dose of up to 1 g or in some instances up to 2 g per patient and treatment may very well be advantageous.

Surprisingly, it has been shown in the present invention that due to the increased ADCC activity the amount of antibody as applied for therapeutic and/or prophylactic purpose can be reduced, yet still leading to positive therapeutic effects even in reduced doses. Due to the increased ADCC activity the amount of antibody applied can be reduced at least 10%, preferably at least 20%, more preferably at least 30%, most preferably at least 50% compared to the dosage regimen for the parental antibody.

Alternatively, the antibody according to the invention can be applied in very high dosages. This is based on the fact that the inventive antibody has reduced CDC activity which is known to cause side effects in individuals. Therefore especially in risk patients who have developed already side effects as a result of application of antibodies for purposes of passive immunotherapy, this surprisingly positive property can be of high advantage.

The treatment preferably is repeated at certain time intervals, according to the half life of the antibody used, which usually is in the range of from 3 to 30 days. By particularly derivatizing the antibody it is possible to increase the half life to up to several months and to thereby lengthen the treatment intervals accordingly. The medicament used according to the invention preferably is provided in a suitable formulation. Preferred are such formulations with a pharmaceutically acceptable carrier. The latter comprises, e.g., auxiliary agents, buffers, salts and preservatives. Preferably, a ready to use infusion solution is provided. Since an antibody is relatively stable, medicaments based on antibodies or their derivatives have the substantial advantage that they can be put on the market as a storage-stable solution, or as a formulation in a ready-to-use form. The former preferably is storage-stable in the formulation at refrigerator temperatures up to room temperature. The medicament used according to the invention may, however, also be provided in frozen or lyophilized form which may be thawed or reconstituted when required.

The concentration of the active substance of the medicament will depend on its tolerability. A particularly well tolerable preparation based on a humanized antibody can be administered directly to the patient at a high concentration without further dilution. By the preferred concentration in the range of from 0.1% to 10%, preferably from 1% to 5%, it is possible to keep low the administered volume and the corresponding time of infusion. Usually, the medicament will be administered i.v. Likewise, however, also another parenteral or mucosal mode of administration can be chosen, which brings the active substance to a systemic or local application at the site of the tumor or of the metastases.

EXAMPLES

The following examples shall explain the present invention in more detail, without, however, restricting it.

BRIEF DESCRIPTION OF THE FIGURES

FIG. 1: Sequences of the humanized light chain variable region (SEQ ID NO:1).

FIG. 2: Sequence of the humanized heavy chain variable region. Either sequence (SEQ ID NO:2) or 2 (SEQ ID NO:3) can be used.

FIG. 3: Binding activity analysis of IGN311 Glyco I compared to IGN311 wt.

FIG. 4: Results of CDC analysis using SKBR 5 cells as target

FIG. 6: Schematic picture of a bi-sected hybrid type N-glycosylated antibody. N-acetylglucosamines are depicted as squares, mannoses are depicted as circles, galactoses are depicted as ellipses.

Example 1

Abbreviations

Figure 5:
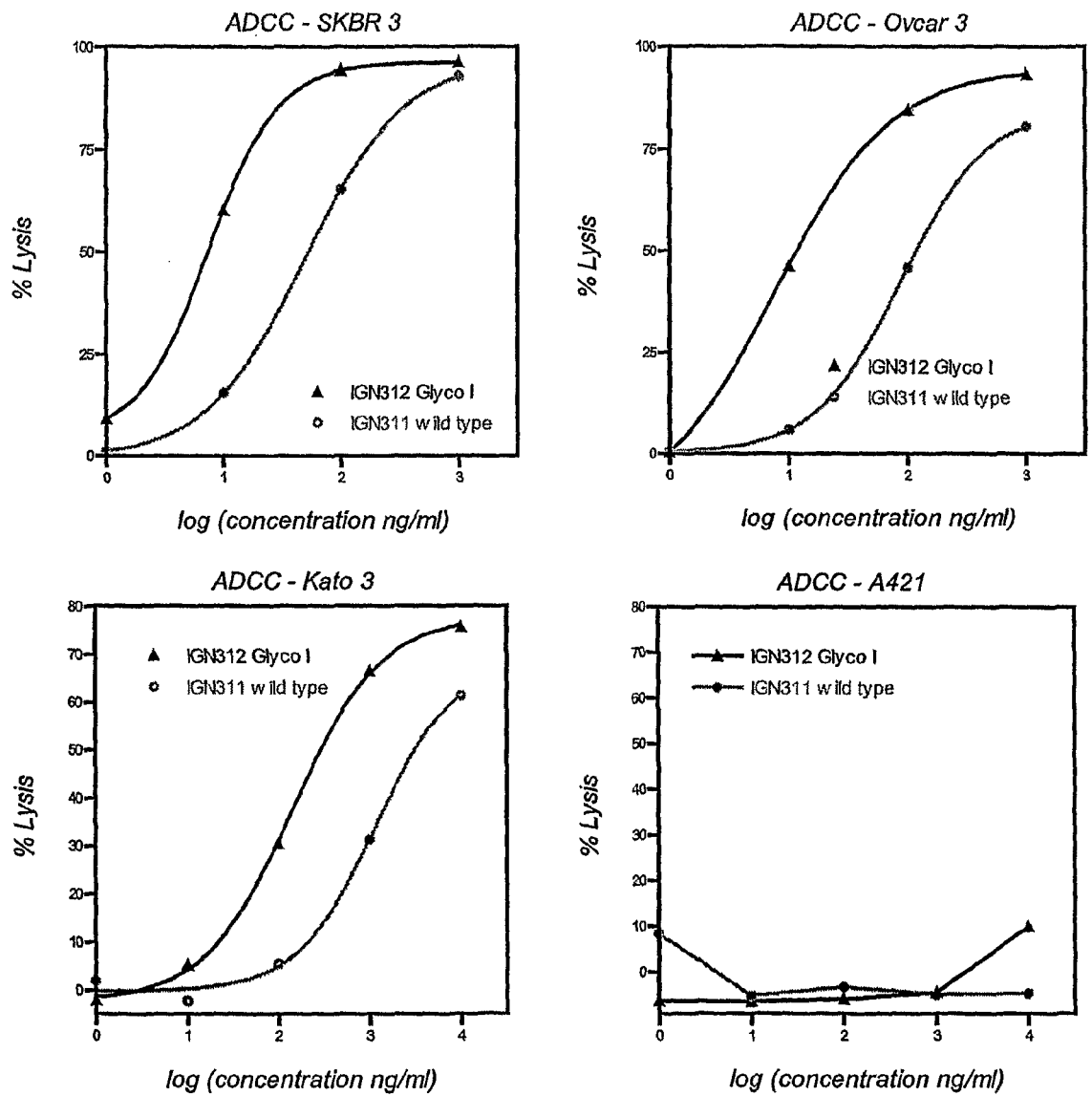
FIG. 5: Results of the ADCC lysis experiments of IGN312 Glyco I on SKBR3, Ovcar 3, Kato III and A421 cells.

SEC-HPLC Size Exclusion Chromatography-High Performance Liquid Chromatography

PBS Phosphate Buffered Saline

SDS-PAGE Sodium-Lauryl-Sulfate-Poly-Acrylamide-Gel-Electrophoresis

ADCC Antibody dependent cellular cytotoxicity

CDC Complement dependent cytotoxicity

IGN311 humanized monoclonal anti-Lewis Y antibody

IGN312 Glyco-engineered humanized monoclonal anti-Lewis Y antibody with identical specificity as IGN311

ELISA Enzyme linked immuno sorbant assay

Methods

SDS-PAGE

Integrity, size and potential degradation products of purified expression product were analyzed by SDS-PAGE. Samples were diluted in 4×NuPAGE SDS sample buffer and incubated at 85° C. for 10 min. 10 µl were loaded on Novex NuPAGE 4-12% Bis-Tris gels (Invitrogen) run in a Novex Electrophoresis unit for 50 min at 200 V and 125 mA. Gels were silver-stained according to the instructions of the manufacturer (Invitrogen).

IEF (Isoelectric Focusing)

Isoform-distribution, degradation and potential deamidation products were analyzed by IEF. After dilution in Novex IEF sample buffer (Invitrogen), samples were loaded on a Novex IEF pH 3-10 Gel and separated according to the instructions of the manufacturer. Gels were silver-stained.

ELISA Based on Anti-idiotypic Antibody Specific for IGN311

Binding activity of the expression product was analyzed by a specific sandwich ELISA by incubating antibody samples in serial dilutions (from 100 pg to 1 µg/ml) in microtiter wells coated with the monoclonal anti-idiotypic antibody MMA383. After blocking with 3% FCS and washing, bound expression product was determined by incubation with goat anti-human IgG+A+M/Peroxidase conjugate (Zymed, Calif.) and developed with o-phenylenediamine/hydrogen peroxide. Measurements were made using an ELISA reader at 492 nm/620 nm. Measured optical densities were plotted versus logarithm of the antibody concentration (ng/ml) and fitted using a sigmoidal four parameter fit. EC50 values were calculated and used for quantification.

CDC

The complement mediated lytic activity was tested in a $^{51}$Cr release assay using the Le-Y antigen-positive SKBR5 breast cancer cell line as target cells. Target cells were incubated for one hour with 100 µCi of $^{51}$Cr, washed twice with medium and plated at a density of $20 \times 10^3$ cells per well into a 96-well microtiter plate together with a serial dilution of the sample to be analyzed (100 ng to 50 µg/ml) and complement serum from a volunteer donor. The test plate was incubated for 1 hour at 37° C. in a $CO_2$ incubator. Supernatants were collected and counted for released $^{51}$Cr (Cs). Values for spontaneous release (Sr) and maximum release (Mr) were measured after incubation of representative samples with medium alone or with detergent (SDS), respectively. Complement mediated cytotoxicity was calculated as percentage of cell lysis 100×(Cs-Sr)/(Mr-Sr). The percent cytotoxicity was plotted versus logarithm of the antibody concentration (ng/ml) and fitted using a sigmoidal four parameter fit. EC50 values were calculated and used for quantification.

ADCC

The cellular mediated lytic potential was tested in a $^{51}$Cr release assay using different Le-Y antigen-positive cancer cell lines as target cells (SKBR3, Kato III and Ovcar 3). Target cells were incubated for one hour with 100 µCi of $^{51}$Cr, washed, and plated at a density of $25 \times 10^3$ cells per well into 96-well mictrotiter plate. Effector cells (peripheral blood mononucleocytes from a volunteer donor) were freshly prepared and added to the target cells to achieve E:T ratios of 40:1 together with serial dilutions (100 pg to 1 µg/ml) of the antibody sample to be analyzed. After incubation at 37° C. for 18 hours in a $CO_2$ incubator, cell supernatants were collected and counted for released $^{51}$Cr (Cs). Values for spontaneous release (Sr) and maximum release (Mr) were measured after incubation of representative samples with medium alone or with detergent (SDS) respectively. Cytotoxicity was calculated as percentage of cell lysis 100×(Cs-Sr)/(Mr-Sr). The percent cytotoxicity was plotted versus logarithm of the antibody concentration (ng/ml) and fitted using a sigmoidal four parameter fit. EC50 values were calculated and used for quantification.

The antibody producing cell line was genetically modified in order to express the glycosyl transferase Gnt-III in order to enhance the biological activity of the antibody. The modification was according to the techniques as described in Sburlati et al (Biotechnol. Prog., 1998, 14, 189-192) or U.S. Pat. No 6,602,684.

In a first setup, heavy and light chain genes of IGN311 were isolated, cloned into an expression vector and transfected transiently into EBNA cells: Genes for Gnt-III transferase expression were co-transfected resulting in a new antibody called IGN312. A control wild-type antibody IGN311 wt. was expressed using exactly the same expression vectors and the same host but without co-transfection of genes for Gnt-III expression. Both expression products were purified to homogenicity using an identical Protein-A based down stream process. Expression products were characterized by SDS-PAGE, IEF and a target antigen specific sandwich ELISA. No degradation products could be detected and target affinity of the glyco-engineered antibody as well as assembling of heavy and light chains was not affected by Gnt-III expression.

Results:

Analysis of the Glycosylated Antibody (IGN312)

Glyco-engineered expression product IGN312 (IGN312 Glyco I) was compared to IGN311 wt. By SDS-PAGE analysis. Under non-reducing conditions, both proteins showed exactly the same bands in the range of nearly 150 kDa corresponding to the expected molecular weight of an intact IgG. Under reducing conditions, protein bands of nearly 50 and 25 kDa could be stained corresponding to IgG heavy and light chains, respectively. No differences between the expression products could be found. No degradation products or aggregates were detected. The glyco-engineered version of IGN311 was an intact and correctly assembled IgG.

Comparison of IGN312 and IGN311 wt. In isoelectric focusing analysis showed exactly the same band distribution between a pI of 7.8 and 8.3. Four protein bands of different pI and different amount could be visualized.

FIG. 3 shows the binding activity analysis of IGN311 Glyco I (black curve) compared to IGN311 wt. (grey curve). Data series were fitted using a four parameter sigmoidal fit.

Antibody specificity of the glyco-engineered product was analyzed by its antigen binding activity in an anti-idiotypic ELISA. Dilution curves are displayed graphically in FIG. 4. All curves showed exactly the same shape and could be overlaid. The same assertion can be made by comparing values of sigmoid curve fit and evaluation at EC50. Results of a sigmoid four parameter fit of data series are shown in Table 1. Normalization of activities on IGN311 wt. resulted in very similar values. No significant changes in affinity could be detected therefore and antigen binding of glyco-engineered product was maintained in the range of the original, not glyco-engineered product.

TABLE 1

Binding activity of IGN312 Glyco I measured by an anti-idiotypic binding ELISA, results of a four parameter sigmoid fit.

|  | IGN311 wt. | IGN312 Glyco I |
|---|---|---|
| Bottom | 96.12 | 77.04 |
| Top | 2063 | 2105 |
| Log EC50 | 1.805 | 1.838 |
| Hillslope | −1.376 | −1.208 |
| EC50 | 63.76 ng/ml | 68.81 ng/ml |
| % | 100 | 108 |

Analysis of effector functions were studied in vitro using three different Lewis-Y positive tumor cell lines as target cells. Expression of the target glycosylation pattern Le-Y was investigated prior lysis experiments by FACS analysis using IGN311 wt. as detection antibody. SKBR 3 showed the most intense Le-Y expression followed by Ovcar 3 and finally Kato III (geometric mean fluorescence: SKBR 3: 1803, Ovcar 3: 361, Kato III: 55). A421 has lost its Le-Y positivity and was used therefore as negative control cell line in our experimental setup. Lyses potential of the glyco-engineered antibody via cellular cytotoxicity and via complement activation was analyzed.

FIG. 4 shows results of CDC analysis using SKBR 5 cells as target. Data series were fitted using a sigmoid four parameter fit (Table 2). Evaluation was performed at EC50 and lyses potential was normalized on the activity of IGN311 wt. Lyses potential of IGN312 Glyco I via complement activation appeared to be nearly 44% reduced. FIG. 4 shows the CDC analysis (Chromium release) on SKBR5 target cells. Complement dependent cytotoxicity of IGN312 Glyco I (black curve) and IGN311 wt. (grey curve) were compared. Data series were fitted (Sigmoid four parameter fit).

TABLE 2

CDC lysis activity of IGN312 Glyco I measured by a chromium release assay using SKBR5 as target cell line. Data values were fitted using a four parameter sigmoid fit.

|  | IGN311 wt. | IGN312 Glyco I |
|---|---|---|
| Bottom | −0.747 | 2.217 |
| Top | 70.92 | 70.13 |
| Log EC50 | 2.743 | 2.998 |
| Hillslope | 3.281 | 2.834 |
| EC50 | 553.1 ng/ml | 996.2 ng/ml |
| % | 100 | 56 |

Results of lyses potential analysis of IGN312 via antibody dependent cellular cytotoxicity (ADCC) was analyzed on SKBR 3, Ovcar 3, Kato III and A421 cells. Results are displayed in FIG. 4. Data series were fitted using a sigmoid four parameter model. Lyses activity via ADCC was calculated by normalization on the activity of IGN311 wt. and evaluation at EC50. Results are displayed in Table 3. Lysis activity of IGN312 Glyco I was significantly enhanced in all cases from 6 to 14 fold in comparison to IGN311 wt. A direct correlation between Lewis-Y antigen density measured by FACS analysis (geometric mean fluorescence: SKBR3: 1803, Ovcar3: 361, Kato III: 55) and enhanced cellular cytotoxicity could not be found. A421 showed, as expected, no lysis at all.

TABLE 3

ADCC analysis on different Lewis-Y positive target cells. Antibody dependent cellular cytotoxicity of IGN312 Glyco I and IGN311 wt. were compared. Data series were fitted using a sigmoidal four parameter fit. Activity was calculated by normalization on IGN311 wt.

|  | IGN311 wt. | IGN312 Glyco I |
|---|---|---|
| SKBR3 | | |
| Bottom | −0.6914 | 4.473 |
| Top | 97.25 | 96.28 |
| Log EC50 | 1.694 | 0.8728 |
| Hillslope | 1.019 | 1.459 |
| EC50 | 49.4 ng/ml | 7.46 ng/ml |
| % | 100 | 662 |
| Kato III | | |
| Bottom | −0.3125 | −2.374 |
| Top | 68.1 | 77.74 |
| Log EC50 | 3.063 | 2.164 |
| Hillslope | 1.019 | 0.9021 |
| EC50 | 1157 ng/ml | 145.9 ng/ml |
| % | 100 | 793 |
| Ovcar 3 | | |
| Bottom | 0.0679 | −14.68 |
| Top | 84.78 | 94.65 |
| Log EC50 | 1.94 | 0.8887 |
| Hillslope | 1.202 | 0.8948 |
| EC50 | 87.15 ng/ml | 7.74 ng/ml |
| % | 100 | 1126 |
| A421 | | |
| Bottom | 0 | 0 |
| Top | 0 | 0 |
| Log EC50 | 0 | 0 |
| Hillslope | 0 | 0 |
| EC50 | 0 | 0 |
| % | 0 | 0 |

FIG. 5 shows results of the ADCC lysis experiments of IGN312 Glyco I on SKBR3, Ovcar 3, Kato III and A421 cells.

Discussion and Conclusion

The data presented in this study indicate that it is possible to enhance the ADCC activity of an IgG1 antibody while lowering the CDC capacity by glyco-engineering. This study showed that genetic engineering of the glycosylation apparatus of an industrial expression cell line can be a very interesting tool for the modulation and fine tuning of the effector functions of an over-expressed antibody. Antibody dependent cellular cytotoxicity could be significantly increased up to at least 20 fold by this principle. The amount of mannosylated hybrid-oligo-saccharide structures increased in parallel which decreased complement activation.

A balanced and stable expression level on Gnt-III transferase would therefore be an essential requirement for the generation of a glyco-engineered therapeutic antibody with enhanced lytic potential. The establishment of a production process based on a stable IGN312 expressing cell line will be the next crucial step in order to finally compare clinically the efficiency of this "new generation antibody".

Example 2

Lysis of Disseminated Tumor Cells Using the Parental Antibody IGN311—Clinical Reports Dosage and Duration of Administration This is a multiple-treatment, escalating dosage study. All subjects received IGN311 on Day 1 and 15. The first three evaluable subjects received 50 mg IGN311 per infusion, the next three evaluable subjects received 100 mg IGN311 per infusion and the last three evaluable subjects received 200 mg IGN311 per infusion.

IGN311 was administered intravenously in a slow infusion during a two hour period.

The subject should not receive any other therapies for the treatment of carcinoma (e.g. chemotherapeutic, radiation, immune therapy or any investigational agent other than IGN311) during the study period with the exceptions of bisphosphonates and hormonal therapy.

Assessment of Disseminated Tumor Cells in Peripheral Blood:

Sample Collection

Blood samples were collected on Day 1 and Day 15 before start of infusion and on Day 43. Blood samples (approximately 28 ml) were collected by a single venous puncture (from the antecubital vein or other suitable site as determined by the investigator) into anticoagulation collection tubes (Vacutainer® tube with EDTA). To avoid the contamination of the blood samples with epithelial cells accumulated during the penetration of the needle through the skin, the first 3 ml blood had to be collected in a separate Vacutainer and had to be discarded. The tumor cell enrichment protocol had to be processed within 2 hours.

Enrichment of Tumor Cells 25 ml cooled peripheral blood were gently filled into the upper compartment of an OncoQuick® tube without disturbing the separation medium underneath the porous barrier and centrifuged at 1600×g and 4° C. for 20 min. After centrifugation, the interphase between the upper plasma (yellow/brownish) and the lower separation medium (blue), containing the tumor cells, were collected and transferred into a new 50 ml centrifugation tube and washed. The cell pellet was then be resuspended in 4 ml washing buffer and centrifuged onto microscope slides.

Results:

It has been shown that the number of tumor cells which had been detected in several sear from patients decreased due to the treatment with IGN311.

---

The invention claimed is:

1. A monoclonal antibody or fragment thereof that recognizes the Lewis Y antigen and is derived from a parental monoclonal antibody that recognizes the Lewis Y antigen, characterized in that the Fc region of said antibody or fragment thereof carries a bi-sected hybrid type N-glycosylation pattern and that said antibody shows at least 10 fold increased ADCC and at least 10% reduced CDC activity as compared to the ADCC and CDC activity of said parental monoclonal antibody, wherein said antibody does not contain a core fucosylation.

2. The antibody according to claim 1, characterized in that the ADCC activity is increased at least 20 fold.

3. The antibody according to claim 1, characterized in that the ADCC activity is increased at least 25 fold.

4. The antibody according to claim 1, characterized in that the ADCC activity is increased at least 40 fold.

5. The antibody according to claim 1, characterized in that the ADCC activity is increased at least 60 fold.

6. The antibody according to claim 1, characterized in that the CDC activity is at least 20% decreased.

7. The antibody according to claim 1, characterized in that the CDC activity is at least 40% decreased.

8. The antibody according to claim 1, characterized in that it carries a bi-secting N-acetylglucosamine group.

9. The antibody according to claim 1, characterized in that it is a humanized antibody.

10. The antibody according to claim 1 which is IgG or a fragment thereof.

11. The antibody according to claim 10 which is IgG1 or a fragment thereof.

12. A pharmaceutical preparation containing an antibody according to any one of claims 1 to 11 in a pharmaceutically acceptable carrier or diluent.

* * * * *